Aug. 7, 1934. E. P. WRAY Plant Pat. 101
STRAWBERRY
Filed Jan. 3, 1933
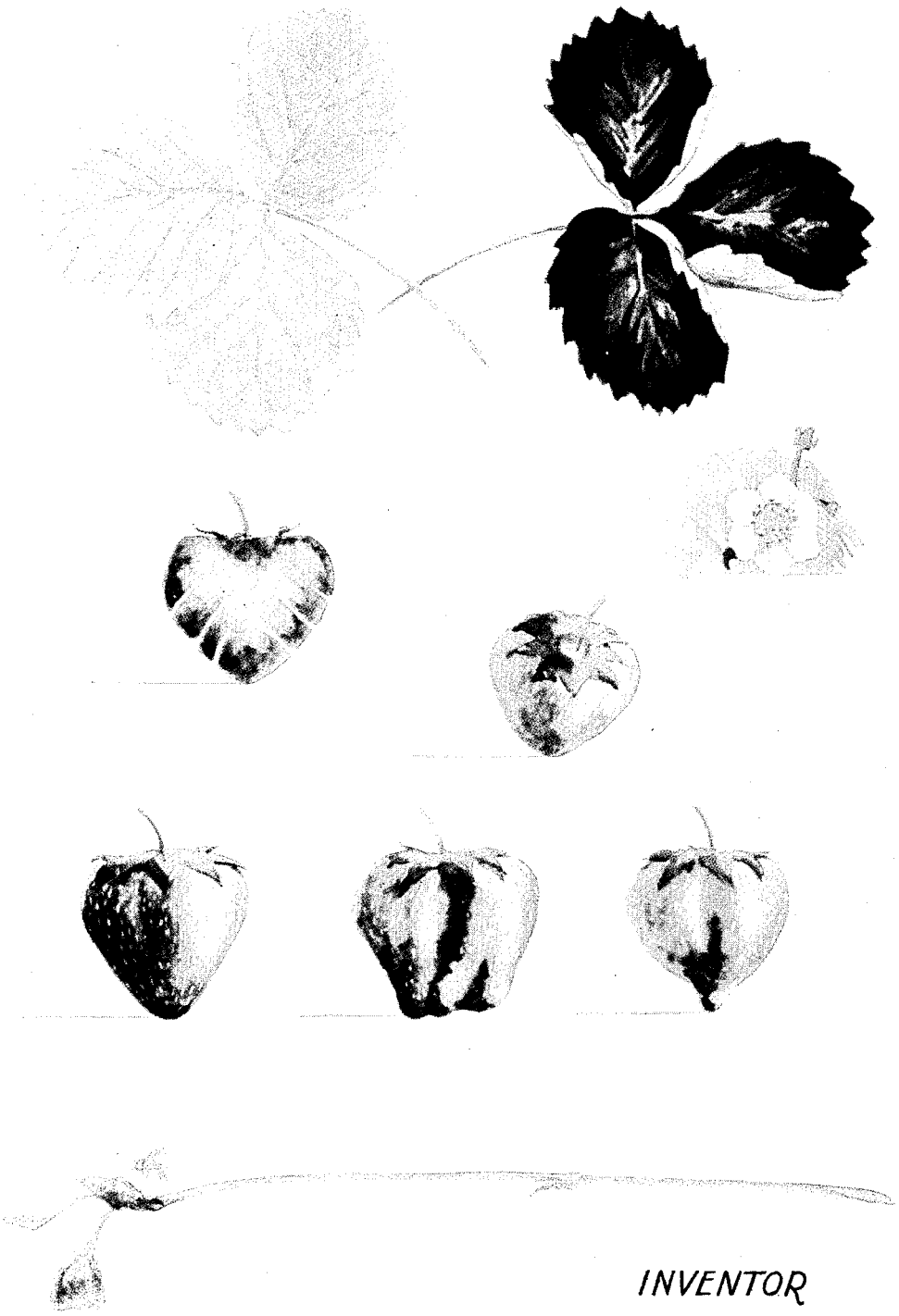
INVENTOR
Edwin P. Wray Patented Aug. 7, 1934

Plant Pat. 101

UNITED STATES PATENT OFFICE

101

STRAWBERRY

Edwin P. Wray, White Salmon, Wash.

Application January 3, 1933, Serial No. 649,964

1 Claim. (Cl. 47—62)

This invention relates to a new and distinct variety of strawberry.

This new variety of strawberry is early, ripening its first fruit in the spring only three days behind Premier. At Kennewick, Washington, where Horace Wray had one half acre in bearing in the spring of 1932, the first commercial picking was made May 15th. It also has a long ripening season as the last picking on this field was made June 10th. The size of the fruit is large to extra large and the production is heavy. In color the fruit is a glossy medium dark red and its flavor is a strong strawberry acid. Its skin is remarkably tough and its flesh is extra solid, red and juicy. If picked when partly red it will ripen up redder inside and out than when allowed to ripen fully on the vine.

Its origin is a seedling cross between Americus and Bedarena (Etter) and this seedling crossed with Chesapeake. The original plant first bore fruit on my farm at White Salmon in the spring of 1929 and its various merits at once attracted my attention. It has since been asexually reproduced each year and its distinctive merits described herein make it worthy of extensive culture.

The drawing obviously shows respectively bottom and top plan views of the leaf, top plan view of a flower, cross-section of a ripe berry, side elevations of several forms of the ripe fruit, and a view of the runner.

*Plant.*—Medium height, a compact strong grower with shiny dark green foliage that stays green until hard freezes in winter. Crown stools out well and throws numerous fruit stems and runners.

*Leaves.*—Medium thick, crinkled, compact and the lobes roundish with medium wide and medium deep serrations. On many of the old leaves and practically all the young leaves the lobes over-lap. Some years about half way up on the leaf stems occasionally is found a little projection that develops into a leaflet. On fertile soil the normal color is a shiny dark green with silvery gray underneath. On weak soil the color is lighter.

*Runners.*—Numerous and rank and noticeable by their red color. The average single runner usually has three plants, but strong runners may have four plants in line besides a branch runner at a joint and several additional plants. The space between plants varies from 8 to 12 inches next to the parent plant down to 3 inches at the tip of the runner. Runners begin to appear in the spring by the time the first berries are ripe and continue their growth into winter if moisture and fertility are available.

*Blossoms.*—Perfect, large and white with a yellowish center and the petals opening with a crinkled appearance. Most of the blossoms open under the leaves and are thus protected from frost. The early blossoms usually have seven petals, but mid-season six petals are more prevalent with the last blocks having five petals. Bees and insects like the blossoms and pollenization is perfect.

*Fruit.*—Large to extra large of the round conic form as represented on page 26 of Farmers Bulletin 1043. However variations of this form include oblate, conic, round and short wedge also as represented on page 26 of Farmers Bulletin 1043 and illustrated also by the accompanying drawing. Large specimens of fruit will measure 1½ to 1¾ inches in diameter and a large average size is sustained until the end of the picking season. All of the conic forms are characterized by a flat base around which a large calyx fits closely, to rise in a crater like ring to form a depression where the stem is attached. Some of the conic form have noticeably straight sides from the thick shoulders at the base to a rounded apex while others have rounded sides with an extended apex. Under normal growing conditions the forms are symmetrical, but in seasons when damaged by severe winter weather or late spring frosts or too cold growing weather the fruit is or may be somewhat ridgy. The fruit is borne on strong upright and horizontal trusses that have clusters of as many as 16 berries which bend to the ground with their heavy load at picking time. Pickers must have sharp finger nails to cut the stems as they will not break or snap off.

The color of the fruit is a uniform glossy, medium dark red and if picked but half red will continue to color up fully inside as well as outside. In warm weather it colors up evenly on the underside where it lies on the ground and its color in the dense shade of the leaves is nearly as dark as in the sunshine. When picked the red graduates to the center where it is lighter; but over night the center darkens also.

Medium large yellow seeds moderately thickly set extend to the contour of the skin. The skin is remarkably tough and has a gloss that lasts several days after the fruit has been picked. Pickers stain their fingers but little and the fruit by not being scarred up retains a good appearance unusually long. This tough skin and solid flesh make this a highly satisfactory shipping berry.

It has a strong strawberry acid flavor, but in reality it is sub-acid and very palatable. On account of this strong flavor, its firmness and color this strawberry is very successfully canned, cold packed or frozen. When canned it has a clear syrup as the seeds do not cook out.

What is claimed is:

The strawberry plant herein disclosed, bearing fruit characterized by its large to extra large conic form, its glossy medium dark red color, its toughness of skin, its strong strawberry acid flavor, its earliness, its firmness, its resistance to frost, its canning qualities and its heavy production.

EDWIN P. WRAY.